United States Patent [19]

Sawada et al.

[11] Patent Number: 4,727,026
[45] Date of Patent: Feb. 23, 1988

[54] METHOD FOR DIRECT SACCHARIFICATION OF RAW STARCH USING ENZYME PRODUCED BY A BASIDIOMYCETE BELONGING TO THE GENUS CORTICIUM

[75] Inventors: Masahiko Sawada, Soka; Kazuhiko Kurosawa, Sapporo; Hiroshi Sasaki, Sapporo; Shoichi Takao, Sapporo, all of Japan

[73] Assignee: Godo Shusei Co., Ltd., Tokyo, Japan

[21] Appl. No.: 866,296

[22] Filed: May 23, 1986

[30] Foreign Application Priority Data

Nov. 26, 1985 [JP] Japan ................................ 60-265261

[51] Int. Cl.$^4$ ........................ C12P 19/20; C12P 19/14; C12N 9/30; C12N 9/34; C12R 1/645
[52] U.S. Cl. ........................................ 435/96; 435/99; 435/203; 435/205; 435/911
[58] Field of Search .................... 435/96, 99, 203, 205

[56] References Cited

U.S. PATENT DOCUMENTS 4,591,560 5/1986 Kainuma et al. ................ 435/96

OTHER PUBLICATIONS

Chemical Abstracts, vol. 91: 156756r (1979).

Primary Examiner—Lionel M. Shapiro
Attorney, Agent, or Firm—Oblon, Fisher, Spivak, McClelland & Maier

[57] ABSTRACT

A method for the cooking-free saccharification of starch using an amylase produced by *Corticium rolfsii* AHU 9627 or its variants. According to the method, even a high viscous suspension of 10% (w/v) or more raw-corn starch is almost completely hydrolyzed within 8 hours. The saccharification is proceeded at a higher temperature and a lower pH compared with those in known methods utilizing other amylases which are able to hydrolyze uncooked starch, so that the propagation of the infectious bacteria which would affect the saccharifying efficiency can be avoided.

2 Claims, 2 Drawing Figures a) Rice, b) Waxy Corn, c) Wheat, d) Tapioca,
e) Sweet Potato, f) Sago, g) Potato

METHOD FOR DIRECT SACCHARIFICATION OF RAW STARCH USING ENZYME PRODUCED BY A BASIDIOMYCETE BELONGING TO THE GENUS CORTICIUM

BACKGROUND OF THE INVENTION (1) Field of the Invention

This invention relates to the saccharification of starchy substances, particulary to the method for glucose production from raw-starch using the enzyme produced by a basidiomycete belonging to the genus Corticium.

(2) Description of the Prior Art

On the manufacturing process of glucose, starchy substances have been saccharified by two-step reactions using two different types of amylases. The process consists of cooking process of starchy substances at elevated temperature, liquefaction of cooked starch by $\alpha$-amylase at a temperature between 80° and 120° C., and saccharification by glucoamylase at a temperature between 45° and 60° C.

This method requires a large amount of thermal energy in the preceding cooking process and some complicated procedures because the optimum temperatures of $\alpha$-amylase and glucoamylase, and the optimum pHs of these enzymes are different, respectively. Furthermore, the cooked starch is so pasty that the enzyme reaction do not proceed uniformly at the concentration between 30 and 50%. From the standpoint of the control of factory, the process involves many difficult problems to be solved.

In order to overcome the above mentioned drawback, it has been made many attempts to saccharify raw-starch without cooking. For this purpose, the enzymes produced by the fungi belonging to the genus Aspergillus and the genus Rhizopus were frequently used. In these methods, glucose can be obtained by one-step reaction and the reaction mixture shows low viscosity even at a higher concentration of starch than 30%. Therefore, the methods provide some advantages in energy cost and operation techniques.

However, most enzymes used in these processes have less activity toward raw starch at a high substrate concentration. According to the report by Ueda et al on the enzymes of *Aspergillus awamori* [Starch, 33(9), 313(1981)] and Rhizopus sp. [Starch, 27, 123(1975)], an upper limit of starch concentration for the saccharification is 2% at the most. Moreover, the enzyme produced by *Chalara paradoxa*, which was reported by Kainuma et al as an active enzyme capable of saccharifying raw starch ["Dempun Kagaku" (Starch Science), 32(3), 189(1985) and Japanese Laid-open patent application No. 59-140896] was able to hydrolyze raw starch only at a concentration less than 5%. These results suggest that enzymatic saccharification of raw starch at a concentration more than 10% is very difficult.

In order to saccharify uncooked starchy substances, attention should be paid to prevent the contamination of various microbials during the reaction. The reaction should be carried out at a temperature as high as possible, preferably at a temperature between 45° and 60° C. The enzymes produced by Rhizopus sp. and *Chalara paradoxa* are inadequate for the saccharification of raw-starch, because they cannot be used at a temperature higher than 50° C.

In recent years, it has been reported that an enzyme produced by a strain of *Corticium rolfsii* (IFO 4878) has some saccharifying activity toward uncooked starch [Nippon Shokuhin Kogyo Gakkaishi, 25 (1), 22 (1978)]. This enzyme has the activity to saccharify about 90% of starch in the reaction mixture containing 10% corn starch (w/v). As they stated in the report, it is believed that there is a limit to achieve effective saccharification of uncooked starch by the enzyme.

As it has been verified by the above mentioned references, there has never been a suitable method for industrial saccharification of starch without cooking.

SUMMARY OF THE INVENTION

The present inventors made extensive studies on the method for the enzymatic saccharification of starch without cooking. As a result, it was found that the enzyme produced by a fungus beloning to the genus Corticium had much higher activity toward uncooked starch than known glucoamylases, and a suspension of 10% (w/v) raw-corn starch was almost completely hydrolyzed by the enzyme within 8 hours. It was also found that the saccharification proceeded at a higher temperature and a lower pH than the other amylases which were able to hydrolyze uncooked starch. These properties are very profitable from the standpoint of controlling the infectious basteria which would effect the saccharifying efficiency.

Particularly, the present invention provides a method for the cooking-free saccharification of starch by an amylase produced by *Corticium rolfsii AHU 9627* or its variants.

DETAILED DESCRIPTION OF THE INVENTION AND PREFERRED EMBODIMENTS

Figure 1:
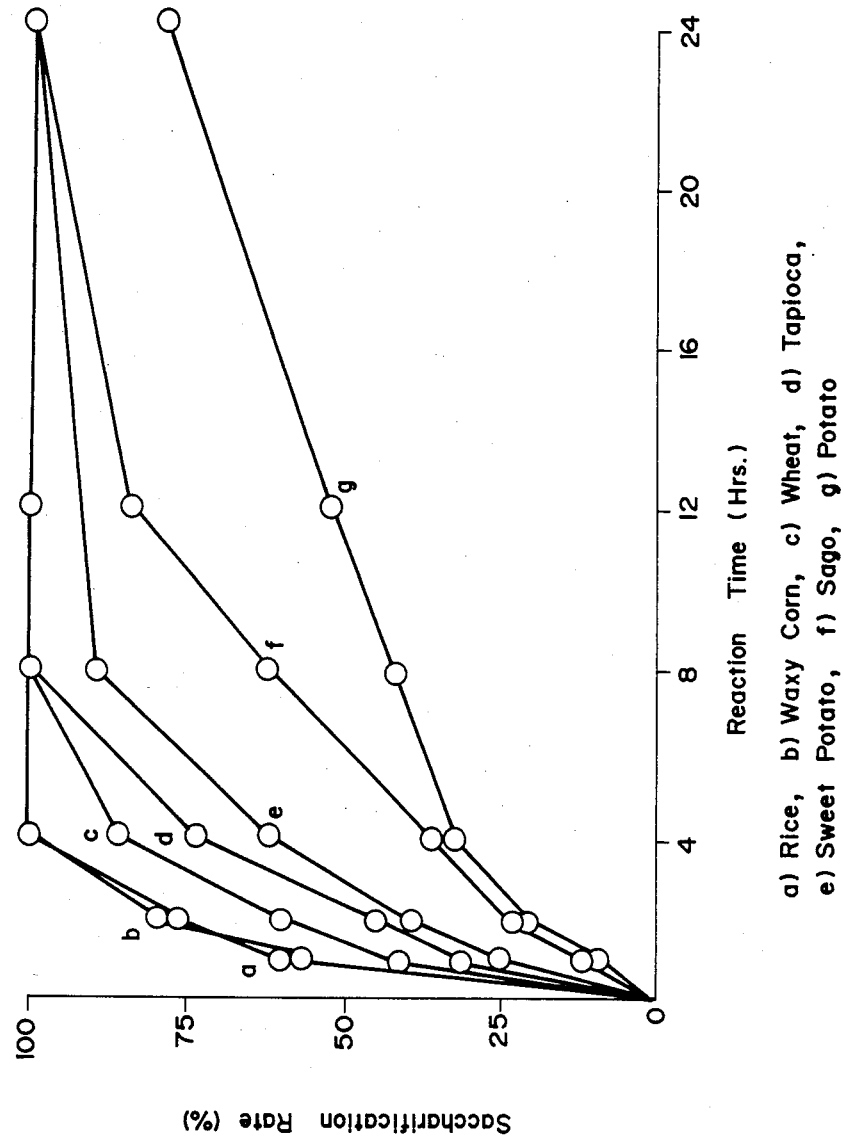
FIG. 1 is a graph showing the relation between saccharification rate and reaction time, when various kinds of raw-starch were saccharified by the invented method (Example 1).

The strain (AHU 9627) used in the present invention, which is able to produce an active amylase capable of saccharifying raw-starch, has the following mycological properties.

(1) Growth on Various Media (i) Growth on malt extract agar and oat meal agar is very good. Colonies reach about 9 cm in diameter in 7 days at 30° C. Plumose white mycelia spread radially on the surface of culture media. Formation of aerial hyphae is remarkable and 300 to 500 sclerotia are formed in a plate (9 cm in diameter). Primary conductive hyphae on the surface of culture media are thick, 4.5 to 9.0 m wide, generally bearing clamp connections at widely spaced septa. Secondary and tertiary hyphae are narrower, and lack clamp connections.

Sclerotia are initially tinged with brown and then gradually turn into blackish brown in color. They are globose, and smooth walled, 1 to 2 mm in diameter.

(ii) Growth on potato dextrose agar is far inferior to that on the above mentioned two media. The surface of the agar medium is covered with mycelia, but aerial hyphae and sclerotia are not formed.

(2) Physiological Properties

Effects of growth temperature and initial pH of the culture media were examined on malt extract agar, oat meal agar and in potato dextrose solution containing 0.1% of yeast extract. The results are as follows:

(i)

Growing temperature range: 5°–50° C.
Optimum growing temperature: 15°–30° C.

(ii)

Growing pH range: 1.5–8.5
Optimum growing pH: 3.0–6.0

(3) Formation of Basidiospores

Immediately after isolation, basidiospores were formed on the agar medium containing 50% of water-extract from tomato stems and leaves. The basidia were clavate to obovoid, 7–9×4–5 μm, sterigmata were 2.5–4.0 μm long and basidiospores were obovoid to clavate, apculate, curved, 4.5–6.5×3.5–4.5 μm.

On the basis of the observations of morphological characteristics, especially formation of sclerotia, clamp connections and basidiospores, and physiological properties, the fungus was identified as *Corticium rolfsii* with reference to "Compendium of Soil Fungi" Academic Press, London (1980) by K. H. Domsch et al, "Genshoku Sakumotsu Byogai Zusetsu" third eddition, Yokendo, Tokyo (1967) by Kitajima et al, "The Genera of Hyphomycetes from Soil" Williams & Wilkins, Baltimore (1968) by G. L. Barron, and Phytopathology, 51, 107–128 (1961).

The strain was an isolate from a tomato stem, *Corticium rolfsii*, is also called by the name of "KOTSUBU KOYAKUTAKE" or "SHIRAKINU BYOKIN" in Japan and it is one of plant pathogens belonging to Basisiomycetes.

*Pellicularia rolfsii, Botryobasidium rolfsii, Corticium centrifugum,* and *Athelia rolfsii* are synonyms for *Corticium rolfsii,* and *Sclerotia rolfsii* is the name given to the anamorph of the fungus.

*Corticium rolfsii* IFO 4878 and IFO 6146 have almost same properties with the present strain, but they show the following morphological differences from the strain used in the present invention.

(a) The present strain forms small sclerotia, almost globose in uniform sizes. As compared with this, the sizes of sclerotia formed by IFO strains are dispersed 0.8–3.5 mm, and the shapes are heteromorphic.

(b) The IFO strains form relatively few sclerotia, 10–100 per plate, (0.2–2 sclerotia/cm$^2$ on average), whereas the present strain forms abundant sclerotia, 300–500 per plate (5–8 sclerotia/cm$^2$ on average).

From the above mentioned characteristics, the present organism were differentiated from IFO strains and determined as a novel strain. Therefore, we referred to this strain as *Corticium rolfsii* AHU 9627 in order to distinguish the strain from the others and deposited the strain in the Fermentation Research Institute, the Agency of Industrial Science of Technology of Japan, by International Deposit No. 1033 (FERM BP-1033).

In order to obtain a useful amylase (hereinafter referred to as present enzyme) in the present invention, the strain is inoculated in the liquid medium containing nutrients and cultured as usual. After incubation, the enzyme capable of saccharifying raw-starch is collected from culture broth.

The enzyme-producing organism includes not only the AHU 9627 strain, but also all strains belonging to the same species and their variants capable of producing the present enzyme.

The artificial variants of the AHU 9627 may be readily obtained by UV irradiation, cobalt 60 irradiation or treatments with chemical variation-inducing agents.

These strains and variants can be grown on the culture media for ordinary basidiomycetes, for example, liquid media, solid media and the like. The following carbon sources are useful for the enzyme production: cooked or uncooked starch made from potato, cassave, rice and the like; refined rice bran; soybean flour; corn meal; disaccharides such as maltose, lactose, sucrose and the like; monosaccharides such as glucose, fructose, mannose and the like; and dextrin. Of these carbon sources, uncooked potato starch scarcely accumulated reducing sugar in culture media even at a high concentration of carbon source and it was selected as the most useful carbon source by the fact that the enzyme production was suppressed if the reducing sugar in the medium exceeded 20 mg/ml.

The useful nitrogen sources for the enzyme production are corn steep liquor (CSL), casein, meat extract, peptone, inorganic ammonium salts and the like. Of these substances, peptone was preferred, because it did not produce mucilageous materials.

In addition to the above nutrients, suitable amounts of inorganic salts such as $KH_2PO_4$, $MgSO_4$, $FeSO_4$, $MnSO_4$, $CaCl_2$, $CoCl_2$, KCl, NaCl and the like, organic trace elements and surfactants such as Tween 40, Tween 80, Span 80 and the like may be added, if they are necessary.

A satisfactory amount of the enzyme can be produced, when the organism is inoculated in the medium containing the above mentioned nutrients and incubated at a temperature between 15° and 30° C., preferably around 27° C., for 5 to 10 days.

The supernatant and concentrate of the culture broth are usable as the enzyme solution, and the enzyme preparations made from the culture supernatant are also useful for saccharification of raw-starch. The enzyme can be partially or completely purified by the following methods: salting-out with ammonium sulfate, sodium chloride and the like, ion-exchange chromatography, isoelectric precipitation, fractionation with solvent, adsorption chromatography and so forth.

The present enzyme has the following properties.

(i) Effect of pH

The present enzyme is active between pH 2.0 and 7.0. The optimum pH for the enzyme activity is 4.0 for raw starch, and 4.5 for gelatinized starch. The present enzyme is stable in the pH range from 3.0 to 7.5, especially from 4.0 to 5.0.

(ii) Effect of temperature

The effect of temperature on the present enzyme activity was examined at pH 4.5 in a solution of 0.05M acetate buffer. The optimum temperature for the present enzyme activity is in the range from 50° to 70° C., especially from 60° to 65° C. In consideration of the enzyme stability, it is in the range from 20° to 60° C., preferably from 40° to 50° C.

(iii) Action on various kinds of raw-starch

The saccharifying ability of the enzyme was examined on various kinds of starch which were made from rice, wheat, sweet potato, waxy corn, tapioca, and sago, at the concentration of 5% at pH 4.0 and 45° C. As a result, it was found that saccharification took place irrespective of the kinds of starch. The data obtained by high performance liquid chromatography showed that the major hydrolyzate was glucose. Saccharifying activity toward gelatinized starch to that toward raw-starch was in the ratio between 1.5 and 2.5 at 40° C., and the value changed a little depending on the pH of reaction mixture and the reaction temperature.

The enzymological differences between the present enzyme and the enzyme produced by *Corticium rolfsii* IFO 4878 (hereinafter referred to as IFO 4878 enzyme) were examined and the following results were obtained. A saccharification test of uncooked starch was conducted at a high concentration, in order to clarify the enzymological differences between two enzymes. The culture supernatant of each strains was partially purified by salting-out with 60% ammonium sulfate. Two enzyme solutions obtained were used for saccharification of 30% corn starch suspension at pH 3.0 and 4.5, and 35°, 45° and 55° C., respectively (Table 1). The figures in Table 1 show the saccharification rate(%) of the two enzymes.

TABLE 1

| Conditions of Saccharification | | Saccharification Rate (%) | | | | | |
|---|---|---|---|---|---|---|---|
| | | Present Enzyme | | | IFO 4878 Enzyme | | |
| Temp. (°C.) | pH | 24 hrs. | 48 hrs. | 72 hrs. | 24 hrs. | 48 hrs. | 72 hrs. |
| 35 | 3.0 | 77 | 83 | 93 | 53 | 53 | 53 |
| | 4.5 | 73 | 85 | 98 | 64 | 67 | 69 |
| 45 | 3.0 | 87 | 100 | 100 | 28 | 45 | 39 |
| | 4.5 | 87 | 100 | 100 | 42 | 45 | 49 |
| 55 | 3.0 | 79 | 81 | 81 | 36 | 36 | 35 |
| | 4.5 | 86 | 86 | 87 | 45 | 45 | 43 |

From the results, it was found that the present enzyme has the ability to hydrolyze raw-starch almost completely at 35° and 45° C. irrespective of the pH of reaction mixture and saccharification rate reduced to 90% at 55° C. The saccharification rate of the IFO 4878 enzyme was about 70% at pH 4.5 and 35° C., but the value reduced to 40 and 50% at 45° and 55° C., respectively. The above results show that the present enzyme is a novel enzyme which has powerful saccharifying activity and high stability to heat compared with the IFO 4878 enzyme.

In order to carry out the present invention, the present enzyme is acted on raw starch.

Almost all kinds of starch made from rice, wheat, corn, waxy corn, potato, sweet potato, tapioca, sago and the like, and materials containing these starch would be usable for the practice of the invention.

Starch is mixed with suitable amounts of the enzyme solution, and then saccharified under the optimum conditions. It is desirable to carry out the reaction in a buffer solution within the pH range from 2.0 to 7.0, preferably from 4.0 to 4.5, and the temperature range from 20° to 60° C., preferably from 40° to 50° C. Any buffer solution may be usable, if it can keep a desired pH range. Acetate-, citrate-, phosphate-, McIlvaine-, tris-malate-buffer solution and so forth may be useful.

The present enzyme is usable in any type of the following preparations: culture broth, extract of the organisms, filtrate of the culture broth, and partially or completely purified enzyme. Of these enzyme preparations, the use of purified enzyme is desirable. In order to determine the optimum amounts of the enzyme for saccharification of raw-starch, it is convenient to measure the activity of the enzyme solution to be used by the following methods.

(1) Saccharifying activity toward raw-starch

The reaction mixture, containing an appropriately diluted enzyme solution and 2.5% raw-nonglutinous rice starch in 0.1M Na-acetate buffer (pH 4.5), was incubated with shaking at 40° C. for 1 hour. After centrifugation, reducing sugar liberated into the supernatant was measured by the DNS method [The Journal of Biological Chemistry 31, 710(1967)]. One unit of the enzyme activity was defined as the amount of enzyme that produced 1 $\mu$mole of glucose per minute under the above mentioned conditions (IU).

(2) Glucoamylase activity

The reaction mixture, containing a diluted enzyme solution and 0.5% soluble starch in 0.05M Na-acetate buffer (pH 4.5), was incubated at 40° C. for 30 minutes. The reducing sugar liberated was assayed by the DNS method and one unit of the activity was defined as the amount of enzyme that liberate 1 mg of glucose in 1 ml of reaction mixture (GU).

It is noted that the activity measured by this method is usable only to make a comparison between the present enzyme and other glucoamylases.

The invented saccharifying method has some advantages that raw-starch suspension can be saccharified even with a high substrate concentration, more than 10%, and that the saccharifying reaction can be carried out at a high temperature under acidic conditions, so that the reaction mixtures can be completely prevented from the contamination of various bacteria. If the enzyme was incubated in combination with alcohol- or organic acid-fermentating microorganisms, the present enzyme will produce alcohols or organic acids very effectively.

The present invention is described by way of examples.

EXAMPLES 1

Inocula were prepared by seeding 3 sclerotia from *Corticium rolfsii* AHU-9627 onto 15 ml of potato dextrose agar containing 0.1% of yeast extract in 9 cm Petri-dishes. After 5 days incubation at 27° C., the organisms on 2 plates were put into a cup together with the agar medium and homogenized in 50 ml of sterilized water. For enzyme production, 3 to 5 ml each of the homogenate was inoculated into 100 ml of liquid medium in 500 ml Sakaguchi-flasks. The medium for enzyme production contains in g/liter: polypepton, 30g; ammonium nitrate, 3.0g; magnesium sulfate, 1.8g; and Tween 80, 1.0g. pH of the culture medium was adjusted to 6.0. Each flask was incubated at 27° C for 7 days. Raw nonglutinous rice starch was sterilized with ethylene oxide, and then aseptically added to the flasks containing the autoclaved medium. After incubation, the culture filtrate was concentrated by ultraconcentration and dialysis (44 IU/ml).

One gram of each starch, made from rice, wheat, waxy corn, tapioca, sweet potato, sago, and potato, was weighed in 100 ml Erlenmeyer-flasks and mixed with 10 ml of 0.1M acetate buffer (pH 4.0) and 10 ml of the enzyme solution, and then the mixture was incubated at 45° C. The reducing sugar liberated was measured by the DNS method. As shown in FIG. 1, each starch, made from rice, wheat, waxy corn, tapioca, sweet potato and sago, was completely saccharified after 12 hour incubation. About 50% of suspended potato starch was hydrolyzed after 12 hour incubation and 80% after 24 hour incubation.

EXAMPLE 2

Eighteen milliliters of a raw-starch suspension in 1M acetate buffer (pH 4.5), which contained 6 g of raw-corn starch, was mixed with 2 ml of the enzyme solution prepared in Example 1 (240 GU/ml) and the mixture was incubated on a shaker at 45° C.

The reducing sugar liberated was determined by the DNS method.

Figure 2:
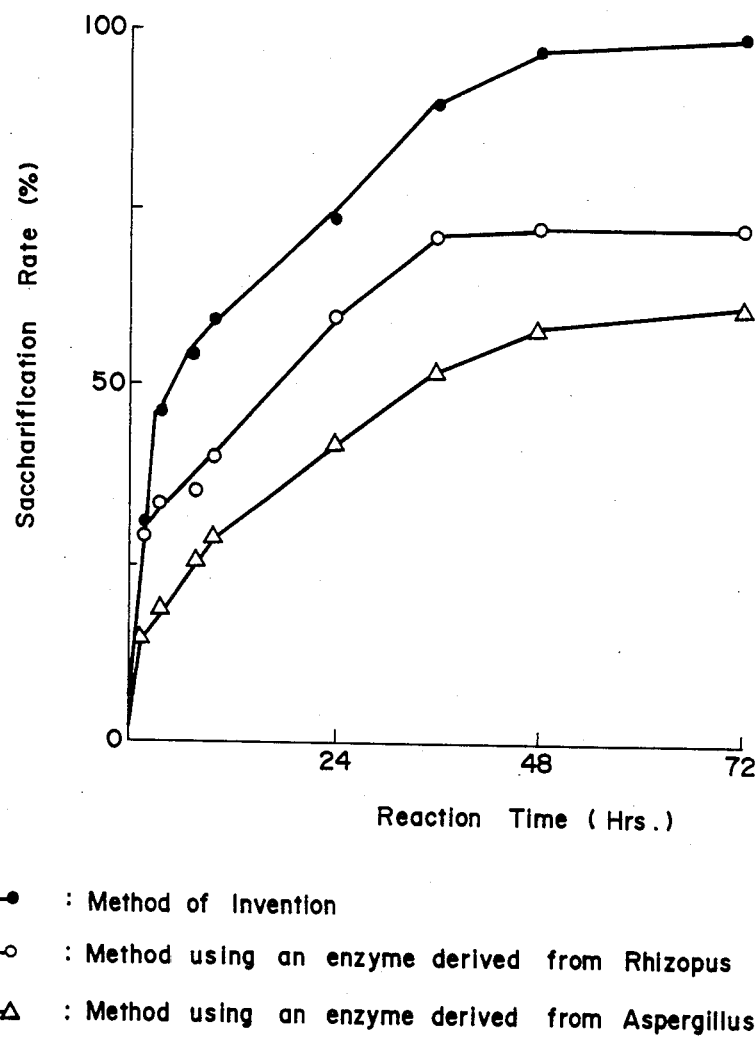
FIG. 2 is a graph showing the relation between saccharification rate and reaction time, when raw-corn starch was saccharified by various kinds of enzymes (Example 2).

As shown in FIG. 2, 73% of the corn starch was hydrolyzed after 24 hour incubation and 98% after 48 hour incubation. The same examination on the commercial glucoamylase preparations showed that the enzymes produced by Rhizopus sp. and Aspergillus sp. hydrolyzed 72 and 58% of the corn starch after 48 hour incubation, respectively.

EXAMPLE 3

Forty grams of raw-sweet potato cut into cylindrical pieces, 1 cm in diameter and 0.5 cm in thickness, were put into a 500 ml flask and mixed with 100 ml of the enzyme solution prepared in Example 1 (22 IU/ml), adjusted pH to 4.0, and then the mixture was incubated at 40° C.

After 48 hour incubation, most of starch in the slices was hydrolyzed and the hard tissues of the slices were changed to spongy pieces. The supernatant of the reaction mixture contained about 9.6 g of glucose per 100 ml.

EXAMPLE 4

One hundred milliliters of a potato starch suspension in 0.1M acetate buffer (pH 6.0), containing 40 g of dried potato starch (Pharmacopoeia), 0.2% (w/w) per starch of heat resistant $\alpha$-amylase, 0.1 g of NaCl and 0.2 g of $Ca(OH)_2$, was heated in boiling water at 95° to 100° C. for 10 minutes, and then autoclaved to prepare a solution of 40% liquefied starch (DE 13.5%).

Fifteen milliliters of the liquefied starch solution and 2 ml of the enzyme solution, prepared in the same manner as in Example 1, in 1M acetate buffer (8 GU/g starch) were mixed and diluted to 20 ml. The mixture was incubated at 45° C. During the course of this experiment, it was found that the liquefied starch was completely hydrolyzed after 48 hour incubation.

What is claimed is:

1. A method for the cooking-free saccharification of starch which comprises using an amylase produced by *Corticium rolfsii* AHU 9627 (International Deposit No. FERM BP-1033) or its variants.

2. A method according to claim 1, wherein a culture filtrate of the *Corticium rolfsii* AHU 9627 (International Deposit No. FERM BP-1033) or its variants is provided as the amylase.

* * * * *